United States Patent [19]

Weisrock et al.

[11] 4,407,950

[45] Oct. 4, 1983

[54] *XANTHOMONAS CAMPESTRIS* ATCC 31602 AND PROCESS FOR USE

[75] Inventors: William P. Weisrock, Tulsa, Okla.; Edward F. McCarthy, Naperville, Ill.

[73] Assignee: Standard Oil Company, Chicago, Ill.

[21] Appl. No.: 167,869

[22] Filed: Jul. 14, 1980

[51] Int. Cl.[3] .................... C12P 19/06; C12N 1/20; C12R 1/64

[52] U.S. Cl. .................................. 435/104; 435/253; 435/910

[58] Field of Search ............................ 435/104, 253

[56] References Cited

PUBLICATIONS

Gaby et al., Journal of Bacteriology, vol. 74, pp. 356–358, (1957).

Gibbs et al., Identification Methods for Microbiologist, vol. A, 1966, pp. 9–14.

Hayward et al., Journal General Microbiol, vol. 26, pp. 133–140, (1961).

Christensen, Jour. Bacteriology, vol. 52, pp. 461–466, (1946).

Ivanoff et al., Jour. Bacteriology, vol. 35, pp. 235–253, (1938).

*Primary Examiner*—Lionel M. Shapiro

*Attorney, Agent, or Firm*—Stephen R. May; Fred E. Hook

[57] ABSTRACT

A new degenerative-resistant strain of *Xanthomonas campestris* is described which is suitable for long-term continuous fermentation to produce xanthan gum from a nutrient medium, typically containing inorganic salts, glucose, $NH_4Cl$, and citric acid, with or without yeast extract or yeast autolysate.

14 Claims, No Drawings

XANTHOMONAS CAMPESTRIS ATCC 31602 AND PROCESS FOR USE

INTRODUCTION

The present invention relates to the production of heteropolysaccharides by the action of certain novel degenerative resistant strains of *Xanthomonas campestris* on aqueous nutrient media. More particularly, it is concerned with the production of xanthan gum by the use of these novel bacteria on an aqueous nutrient medium containing assimilable sources of carbon, nitrogen and inorganic substances.

BACKGROUND

Batch fermentation of an inoculated medium with *Xanthomonas campestris* NRRL B-1459 for 36–72 hours under aerobic conditions results in the formation of xanthan gum, which is separated from the other components of the medium by precipitation with acetone or methanol in a known manner. Because of time required to ferment each batch, the low biopolymer content of the fermented medium and the processing required for the recovery and purification of the product, xanthan gum produced by batch fermentation, hereinafter also referred to as xanthan, is relatively expensive.

Because continuous operation of a fermentation process offers a number of potential advantages over conventional batch methods that could be reflected in lower costs, considerable effort has been put forth in the past to perfect conditions that would support a reliable continuous process. But even with a continuous process a cheap medium from which xanthan can be produced is required. In addition to the necessity of an inexpensive medium in the manufacture of a low cost xanthan product, the ratio of xanthan to cells (bacteria) should be as high as possible in order to reduce subsequent filtration costs for cell removal. The specific productivity of the culture employed also should be as high as possible in order to maintain the aforesaid high ratio as well as to reduce vessel volume and capital costs. The expression "specific productivity" as used in the present description is intended to mean the number of grams of xanthan produced/gram of cells/hour. The culture should be stable under continuous culture conditions on a long term basis to avoid frequent restarts and lost productivity.

Although xanthan has been produced by continuous fermentation in the past, such methods have not met with unqualified success. In some cases, vitamins and/or amino acids had to be employed in the medium in substantial quantities in order to avoid culture degeneration or to improve specific productivity. Use of these additives, as well as soybean protein, cotton seed protein, etc., all tend to make the xanthan thus produced more costly.

It is well known that the continuous production of xanthan by the use of *Xanthomonas campestris* B-1459 has been hampered by a tendency of the culture to change or degenerate after a fairly small and specific number of turnovers, the time during the fermentation to completely replace one volume of broth in the fermentation vessel. Normally, 6–9 turnovers are the maximum that can be obtained before degeneration of the culture occurs. At the same time, there is a decrease in viscosity, a loss in volumetric productivity of xanthan, i.e., grams of xanthan/liter of broth/hour, and appearance of a variety of culture variants or strains that no longer produce xanthan or else produce a xanthan of low quality. It has been demonstrated that culture degeneration occurs when dried distillers solubles (DDS) are used in the nutrient medium as the complex nitrogen source, whether in the whole form or as a water soluble extract. In other cases, certain strains of *Xanthomonas* have been grown successfully without culture degeneration in simple minimal media, but the xanthan:cell ratio and specific productivity have been low, on the order of 0.1–0.12 gram xanthan/gram of cells/hour.

Earlier work has indicated that heteropolysaccharides produced by the action of *Xanthomonas* bacteria on carbohydrate media have potential applications as film forming agents, as thickeners for body building agents in edible products, cosmetic preparations, pharmaceutical vehicles, oil field drilling fluids, fracturing liquids and similar compositions and as emulsifying, stabilizing and sizing agents. Heteropolysaccharides, particularly xanthan gum, have significant potential as a mobility control agent in micellar polymer flooding. This gum has excellent viscosifying properties at low concentration, is resistant to shear degradation and exhibits only minimal losses in viscosity as a function of temperature, pH and ionic strength. For these reasons, xanthan gum is an attractive alternative to synthetic polyacrylamides for enhanced oil recovery operations.

SUMMARY OF THE INVENTION

We have now discovered a degenerative-resistant strain of *Xanthomonas campestris* and have developed a process for using this strain to effectively overcome the problems of continuous xanthan production recited above. This strain of *Xanthomonas campestris* which we have designated *Xanthomonas campestris* P-107 ATCC 31602 is capable of continuously producing xanthan at high specific productivities, i.e., 0.24 to 0.32 gram xanthan/gram cells/hr., for several hundred hours without culture degeneration from an inexpensive aqueous nutrient medium for example, a minimal medium typically consisting primarily of inorganic salts, glucose and NH$_4$Cl. The medium may or may not also contain a yeast extract or yeast autolysate as a supplemental nitrogen source. Generally, it may be said that any medium having assimilable sources of carbon, nitrogen and inorganic substances serves satisfactorily for use with this new organism to produce xanthan.

The process of our invention in which this variable strain is utilized can be either a single stage or two-stage continuous fermentation process. In the single stage embodiment the organism is grown, preferably under conditions such that the quantity of one of the growth nutrients present is limited. The quantity of biopolymer obtained will be determined by the concentration of the limiting nutrient. A portion of the residual glucose or equivalent sugar present is converted to xanthan gum and the latter ultimately recovered from the fermentation effluent. In the two-stage process, the aforesaid fermenter effluent is taken to a second fermentation stage where additional glucose or equivalent sugar is introduced and converted to xanthan. In operation of the second stage, a balance of the flow of the first stage effluent and glucose solution must approximate the flow rate of the second stage effluent. The growth limiting nutrients normally employed are nitrogen, phosphorous or sulfur.

SPECIFIC EMBODIMENTS OF THE INVENTION

Subcultures of this living organism can be obtained upon request from the permanent collection of the American Type Culture Collection, 12301 Parklawn Dr., Rockville, MD 20852. The accession number in this repository for *Xanthomonas campestris* P-107 is given above. The novel *Xanthomonas campestris* strain referred to was isolated from a pilot plant run in which a 28 liter fermenter was operated using a culture of *Xanthomonas campestris* NRRL B1459, growing in a minimal medium having a composition as shown in Table I:

TABLE I

| Component | Concentration (ppm) |
|---|---|
| Glucose | 22,000 |
| $NH_4Cl$ | 300 as N |
| KOH | 1000 + as K |
| $H_3PO_4$ | 300 as P |
| $MgSO_4$ | 100 as Mg |
| $CaCl_2$ | 10 as Ca |
| NaCl | 10 as Na |
| $FeSO_4$ | 2 as Fe |
| $ZnSO_4$ | 0.35 as Zn |
| $MnSO_4$ | 0.35 as Mn |
| $Na_2MoO_4$ | 0.21 as Mo |
| $H_3BO_3$ | 0.07 as B |
| KI | 0.14 as I |
| $CuSO_4$ | 0.020 as Cu |
| Citric Acid | 250 |

Continuous fermentation of the above medium was initially conducted at 28° C., a pH of 6.8, an aeration rate of 0.2–0.4 vol./vol./min., agitation rate of 230 rpm, dissolved oxygen of 90% saturation, and a dilution rate of 0.08 $hr^{-1}$. After about 6 turnovers, the culture began to degenerate with lowered xanthan productivity and viscosity. At this point, several changes were made to the medium. The pH was lowered to 6.4 from 6.8; iron, copper and zinc concentrations in the broth were raised to 3, 0.6 and 1 ppm, respectively, by adding these trace elements to the glucose feed tank (they were previously added with the rest of the inorganic salts), the citric acid level was doubled to 500 ppm, and $H_3PO_4$ and $MgSO_4$ levels were reduced by half. For 2 to 3 culture turnovers after these changes the culture continued to degenerate with viscosity dropping to 70 cp and specific productivity decreasing to 0.07 gram/gram cells/hr.

During an overnight period, the exit line from the fermenter plugged and the culture went into a semi-batch/low dilution rate condition for about 10 hours. The following morning, viscosity was up to 300 cp and when level and flow rates were corrected, it continued to increase. For the next 10 turnovers, specific productivity gradually increased to over 0.35 gram of xanthan/gram cells/hour, and culture morphology became normal again. The culture was maintained at this high productivity for some 30 turnovers after recovery without any evidence of culture degeneration before being terminated by a pH upset. This highly productive culture was saved in a viable state and used to isolate the novel *Xanthomonas campestris* strain referred to above.

After standard plate counts were made on the culture, using YM agar (Difco), 9 isolated colonies of varying sizes were picked and subcultured on YM agar for purification. Three isolates were discarded as obvious duplicates, and the remaining six isolates (one of which was P-107) were maintained for three bi-weekly transfers on YM agar slants. The isolates were then subcultured to EMSY-1 broth and then maintained on EMSY-1 agar slants as well as on the YM agar slants. In addition, cultures grown in EMSY-1 broth were frozen in liquid nitrogen. The composition of this (EMSY-1) broth is given in Table II.

TABLE II

| Component | Concentration (ppm) |
|---|---|
| Glucose | 10,000 |
| $NH_4Cl$ | 112 as N |
| $KH_2PO_4$ | 386 as P |
| $Na_2HPO_4$ | 390 as P |
| $MgSO_4.7H_2O$ | 40 as Mg |
| $CaCl_2.2H_2O$ | 10 as Ca |
| NaCl | 10 as Na |
| $FeCl.6H_2O$ | 1 as Fe |
| $ZnSO_4.7H_2O$ | 0.33 as Zn |
| $MnSO_4.H_2O$ | 0.1 as Mn |
| $Na_2MoO_4.2H_2O$ | 0.067 as Mo |
| $H_3BO_3$ | 0.033 as B |
| KI | 0.033 as I |
| $CuSO_4.5H_2O$ | 0.2 as Cu |
| Citric Acid | 500 |
| Yeast Extract | 400 |

The P-107 isolate was maintained by itself due to its large colony size and apparent similarity to the parent strain, *Xanthomonous campestrix* B-1549. *Xanthomonas campestris* P-107 is understood to be the same strain as P-107.

STRAIN DESCRIPTIONS

The above-mentioned strain of *Xanthomonas campestris* was characterized with respect to *Xanthomonas campestris* NRRL B-1459 from which it was originally derived. The following description characterizes the new strain P-107 ATCC 31602:

I. Cell Morphology

1. After growth in EMSY-1 broth for 18 hours at 28° C., cells appear singly and in pairs. Chain formation is rare. Cell dimensions are 0.3–0.6 microns in width by 0.5 to 2.0 microns in length.
2. After growth in YM broth (Difco) for 18 hours at 28° C., cells appear singly and in pairs, with frequent chaining of 3–5 cells. Cells in YM broth are larger than EMSY-1 broth and have dimensions of 0.5–1.0 microns in width by 1.5–3.0 microns in length. Chains of 5–30 microns may be formed.
3. Strain P-107 does not exhibit motility, has a negative Gram stain reaction, and does not form endospores. These bacteria may be reproduced only asexually by means of binary fission.

II. Colony Morphology

1. After 72 hours growth at 28° C. on EMSY-1 agar plates isolated colonies are creamy colored, circular, entire, raised and mucoid. Colony diameter is 3–4 mm.
2. After 72 hours growth at 28° C. on YM agar (Difco) plates, isolated colonies are yellow in color, raised, circular, entire and mucoid. Colony diameter is 4–5 mm.
3. After 72 hours growth at 28° C. on Nutrient Agar (Difco) containing 1% dextrose, isolated colonies are yellow in color, circular, raised, entire and mucoid. Colony diameter is 2–3 mm.

III. Biochemical Characteristics

In order to determine whether strain P-107 is physiologically different from *Xanthomonas campestris* strain NRRL B-1459, the following tests were conducted.

1. Growth at 35° C. Inoculated slants of YM agar (Difco) and EMSY-1 agar (see Table II for composition) were incubated at 35° C. for five days and the results are shown in Table III.

TABLE III

| Strain No. | YM Agar* | EMSY-1 Agar* |
|---|---|---|
| P-107 | 1+ | 0 |
| B-1459 | 2+ | 0 |

*0 = no growth;
1+ = slight growth;
4+ = heavy growth

2. Growth Characteristics in Minimal Medium. Inoculated tubes of liquid EMS-2 medium shown in Table IV were incubated at 28° C. for 96 hours. Strain P-107 showed heavy growth throughout the tubes with a ragged surface pellicle and clumping in the broth. Strain B-1459 showed less growth overall and only a slight surface growth.

TABLE IV

| Component | Concentration (ppm) |
|---|---|
| Glucose | 22,500 |
| NH$_4$Cl | 224 as N |
| KH$_2$PO$_4$ | 150 as P |
| MgSO$_4$.7H$_2$O | 40 as Mg |
| CaCl$_2$.2H$_2$O | 10 as Ca |
| Citric Acid | 500 |
| FeCl$_3$.6H$_2$O | 2 as Fe |
| ZnSO$_4$.7H$_2$O | 0.66 as Zn |
| CuSO$_4$.5H$_2$O | 0.4 as Cu |
| MnSO$_4$.H$_2$O | 0.2 as Mn |
| Na$_2$MoO$_4$.2H$_2$O | 0.13 as Mo |
| H$_3$BO$_3$ | 0.066 as B |
| KI | 0.066 as I |
| NaCl | 10 as Na |

3. Hydrolysis of Gelatin, Casein, and Starch. Solid agar media individually containing 0.4% gelatin, 0.4% casein, or 0.3% soluble starch were prepared and used according to the procedure in "Identification Methods for Microbiologists," 1966, B. M. Gibbs and F. A. Skinner, eds., Academic Press, p. 12. The results are shown in Table V.

TABLE V

| Strain No. | Gelatin | Casein | Starch |
|---|---|---|---|
| P-107 | 4+ | 3+ | 4+ |
| B-1459 | 4+ | 4+ | 4+ |

Strain B-1459 showed complete hydrolysis of all three substrates, whereas P-107 showed a lesser degree of hydrolysis of casein.

4. Action on Litmus Milk. Cultures inoculated into Litmus Milk medium (Difco) were incubated at 28° C. for three weeks, according to the method of Ivanoff et al. (1938, J. Bacteriol. 35 235). Strains P-107 and B-1459 were active on litmus milk with peptonization, litmus reduction, and precipitate formation.

5. Hydrogen Sulfide Production. A peptone-water medium for H$_2$S production was prepared according to the method of Hayward and Hotchkiss (1961, J. Gen. Microbiol. 26, 133-140). H$_2$S production was determined by the use of lead acetate paper strips suspended over the medium in loosely capped tubes. The cultures were incubated for six days at 28° C. and observed for blackening of the strips. Both strains produced hydrogen sulfide.

6. Urease Production. Urea medium was prepared according to the method of Christensen (1946, J. Bacteriol. 52 461-466). The slants were inoculated and incubated at 28° C. for 14 days. A red to violet color in the medium would be indicative of urea hydrolysis. Urease production was found to be negative for both strains tested.

7. Growth in Presence of Salt. Basal media containing NaCl at concentrations of 1, 2, 3, 4, and 5% were prepared according to the method of Hayward and Hotchkiss (1961. J. Gen. Microbiol. 26 133-140). Cultures were inoculated and incubated at 28° C. for 14 days. Both strains tested gave an identical growth pattern as shown in Table VI.

TABLE VI

| Strain No. | Salt Conc'n* | | | | |
|---|---|---|---|---|---|
| | 1% | 2% | 3% | 4% | 5% |
| P-107 | 4+ | 3+ | 3+ | 2+ | 0 |
| B-1459 | 4+ | 3+ | 3+ | 2+ | 0 |

*0 = no growth;
1+ = slight growth;
4+ = heavy growth

8. Carbohydrate Assimilation Pattern. A basal carbohydrate assimilation medium was prepared according to the method of Hayward and Hotchkiss (1961, J. Gen. Microbiol. 26 133-140). Each strain was inoculated into replicate tubes containing the carbohydrates shown in the Table VII below, and incubated for 14 days at 28° C.

TABLE VII

| Carbohydrate | P-107 | B-1459 |
|---|---|---|
| Glucose | + | + |
| Galactose | + | + |
| Arabinose | + | + |
| Mannose | + | + |
| Cellobiose | + | + |
| Sucrose | weak | weak |
| Fructose | weak | weak |
| Trehalose | + | + |
| Xylose | − | − |
| Mannitol | + | + |
| Lactose | − | − |
| Maltose | + | + |

As can be seen in Table VII, each strain gave an identical assimilation profile.

9. Oxidase Production. Using isolated colonies from 72 hour old YM agar (Difco) plates, the strains were tested for presence of indophenol oxidase using the method of Gaby and Hadley (1957. J. Bacteriol. 74 356-358). Each strain was positive for oxidase, although strain P-107 gave a weaker reaction than B-1459.

10. Catalase Production. Growth from a 48 hour YM agar (Difco) slant was tested for catalase activity by emulsifying a loopful of culture in a drop of 3% H$_2$O$_2$ and observing for effervescence. Strains P-107 and B-1459 were both weakly positive.

11. Utilization of Organic Acids. EMS-2 basal medium without glucose (see Table III for composition) was prepared. Replicate tubes containing 1% citric, malic, succinic, benzoic, and tartaric acids were inoculated and incubated at 28° C. for 14 days and observed for extent of growth. As shown by the result given in the Table VIII below, both strains were identical.

TABLE VIII

| Organic Acid | P-107 | B-1459 |
|---|---|---|
| Citrate | 3+ | 3+ |
| Malate | 4+ | 4+ |
| Succinate | 4+ | 4+ |

TABLE VIII-continued

| Organic Acid | P-107 | B-1459 |
|---|---|---|
| Benzoate | 0 | 0 |
| Tartarate | 1+ | 1+ |

*0 = no growth;
1+ = slight growth;
4+ = heavy growth

12. Indole Production: The strains were tested for indole production in the same peptone-water medium used to test for $H_2S$ production, following the method of Hayward and Hotchkiss (1961. J. Gen. Microbiol. 26 133-140). Both strains were negative for indole production.

13. Acetoin Production. The strains were tested for acetoin production using MRVP medium (Difco) after incubation of the inoculated cultures for six days at 28° C., following the method given in the reference in (12) above. Neither strain tested positive for acetoin.

SUMMARY OF CHARACTERIZATION STUDIES

Strain P-107 is essentially indistinguishable from *X. campestris* strain NRRL B-1459 on the basis of cell morphology. However, definite differences in colonial morphology make this strain distinguishable from B-1459.

Strain P-107 produces larger, paler yellow colonies than does B-1459 on all media which were tested.

In terms of physiological characteristics, this strain is very similar to NRRL B-1459 except that B-1459 grows poorly on a minimal medium. P-107 shows only slight growth on YM agar at 35° C., hydrolyzes casein less actively than B-1459, and exhibits a weak oxidase reaction.

The foregoing is intended to point out that, while the major distinguishing characteristics of this strain lie in its high xanthan specific productivity and resistance to degeneration in continuous culture, other distinguishing characteristics nevertheless are present.

In carrying out the process of the present invention, the fermenter medium is seeded with an inoculum of culture grown in the same medium as that to be used for fermentation at an inoculum level of 5-10% of the medium volume. The culture is grown in a batch mode for 24-48 hours, until a desired cell concentration is reached (usually 1.5-2.5 grams cells/liter). Thereafter, continuous flow of medium is started into the fermenter such that the dilution rate is 75% or less of the specific growth rate at which the organism is growing at that point. Continuous harvesting of a volume of culture broth equal to the volume of medium introduced is also carried out. After approximately two culture turnovers, the dilution rate is adjusted as desired. Xanthan gum, which exists in the recovered broth, can be used without further purification, or filtered to remove cells, or can be precipitated with an alcohol, such as ethyl or isopropyl alcohol, with or without initial cell removal. The medium used in this process is preferably a minimal medium consisting primarily of inorganic salts, $NH_4Cl$, glucose, and citric acid, with or without additional yeast extract or yeast autolysate.

The term "minimal medium" as used throughout the present description and claims should be interpreted to cover media of the type generally referred to herein and specifically in the Examples, together with modifications apparent to those skilled in this field.

Operating conditions to be employed in the process of our invention include the following:

| Agitation | 100-2000 rpm |
|---|---|
| Preferably | 500-1000 rpm |
| Air Rate | 0.2-2 vol./vol./min. |
| Preferably | 0.5-1 vol./vol./min. |
| Temperature | 20-35° C. |
| Preferably | 25-30° C. |
| pH | 5-8 |
| Preferably | 6.4-7.4 |
| Dissolved Oxygen | 10-90% saturation |
| Preferably | 20-60% saturation |
| Dilution Rate | 0.01-0.15 $hr^{-1}$ |
| Preferably | 0.04-0.1 $hr^{-1}$ |

Our invention will be illustrated by reference to the following specific examples:

EXAMPLE I

This Example shows that when *Xanthomonas campestris* NRRL B-1459 is grown in a minimal medium in continuous culture, the organism exhibits only low specific productivity and degenerates in a short time. The culture was grown in a 28 liter fermenter in a minimal medium having a composition shown in Table IX.

TABLE IX

| Component | Concentration (ppm) |
|---|---|
| Glucose | 22,000 |
| $NH_4Cl$ | 300 as N |
| KOH | 1,000 as K |
| $H_3PO_4$ | 150 as P |
| $MgSO_4$ | 40 as Mg |
| $CaCl_2$ | 10 as Ca |
| NaCl | 10 as Na |
| Citric Acid | 500 |
| $FeSO_4$ | 3 as Fe |
| $ZnSO_4$ | 1 as Zn |
| $MnSO_4$ | 0.3 as Mn |
| $Na_2MoO_4$ | 0.2 as Mo |
| $H_3BO_3$ | 0.1 as B |
| KI | 0.1 as I |
| $CuSO_4$ | 0.6 as Cu |

*Xanthomonas campestris* B-1459 was maintained on YM agar (Difco) slants at 4° C. and transferred to fresh agar slants at bi-weekly intervals. For inoculum preparation, a loopful of culture from a fresh (<3 day old) slant was inoculated into a 16×125 mm tube containing 7 ml of YM broth. The culture was incubated at 28° C. on a rotary shaker at 150 rpm, at a 20° inclination for 18 hours. At this point, the contents of the tube were transferred to 50 ml YM broth in a 500 ml Erlenmeyer flask, and incubated at 28° C. on a rotary shaker at 250 RPM for 18-24 hours. Next, the contents of the flask were transferred to a 2000 ml Fernbach flask containing 700 ml of a mineral salt-glucose-$NH_4Cl$ medium, of the composition given above in Table IX. This was incubated under the same conditions as for the 50 ml flask, but for a total of 40 hours. Next, the entire culture was used to inoculate 20 liters of the same medium contained in a 28 liter New Brunswick fermenter (Model CMF-128S). The initial operating conditions employed were as follows:

| Temperature | 29° C. |
|---|---|
| pH | 6.0 |
| Agitation | 230 rpm |
| Air Rate | 0.2-0.4 vol/vol/min |

| -continued | |
|---|---|
| Dissolved O$_2$ | 90% saturation |

After an initial growth lag of about 30 hours, cell growth proceeded over the next 30 hours. When the cell concentration reached 0.9 gm/liter, continuous operation was started at an initial dilution rate of 0.07 hr$^{-1}$. Within 48 hours, the cell concentration rose to 2.5 gm/liter. After about 10 culture turnovers, the viscosity and specific productivity started to decline and were eventually almost totally lost. Cell morphology became abnormal and gum quality deteriorated badly. All of these changes proved to be irreversible and the culture did not revert to normal. A summary of the data obtained in this run is given in Table X.

tion, the temperature was held at 29° C.; the pH at 6.0 to 6.5; agitation in the range of 260–390 rpm, depending on viscosity; the air rate was maintained at 0.1 to 0.18 vol/vol/min; and dissolved oxygen ranged between 40 and 70% of saturation. In this run, the continuous culture of *Xanthomonas campestris* P-107 ATCC 31602 was conducted for 300 hours (14 culture turnovers). After about 60 hours, the xanthan specific productivity increased to 0.17–0.18 gm/gm cells/hour and increased again up to 0.31 gm/gm cells/hour. The run was stopped at 14 turnovers only because a yeast contaminant lowered the performance of the culture. The data for this run are given in Table XI.

TABLE XI

| Time Period (Hrs) | Cell Conc'n (gm/l) | Xanthan Conc'n (%) | Viscosity (cp) | Xanthan Volumetric Productivity (gm/l/hr) | Xanthan Specific Productivity (gm/gm cells/hr) | Dilution Rate (hr$^{-1}$) | Total Culture Turnovers |
|---|---|---|---|---|---|---|---|
| 0–40 | .85–1.7 | .19–.54 | 72–2660 | .09–.18 | .11 | .034–.038 | 0–2.2 |
| 40–192 | 1.74–2.19 | .86–1.0 | 3340–3928 | .17–.25 | .17–.25 | .042–.049 | 2.1–9.0 |
| 192–257 | 2.0–2.2 | 1.15–1.35 | 3680–3920 | .55–.65 | .28–.31 | .045–.048 | 9–12 |
| 157–300 | 2.2–3.4 | 1.02–1.11 | 3332–5080 | .44–.5 | .13–.23 | .04–.049 | 12–14 |

This example illustrates the fact that strain ATCC 31602 is a high productivity variant and can be grown at high specific productivity without culture degeneration in media of the type described herein.

TABLE X

| Time Period (Hrs) | Cell Conc'n (gm/l) | Xanthan Conc'n (%) | Viscosity (cp) | Xanthan Volumetric Productivity (gm/l/hr) | Xanthan Specific Productivity (gm/gm cells/hr) | Dilution Rate (hr$^{-1}$) | Total Culture Turnovers |
|---|---|---|---|---|---|---|---|
| 0–34 | 1.3–1.9 | .26–.30 | 120–340 | .20 | .11–.15 | .07–.08 | 0–2.5 |
| 34–130 | 2.6–2.56 | .32–.39 | 640–850 | .23–.31 | .10–.13 | .07–.085 | 2.5–9.7 |
| 130–178 | 1.7–2.17 | .23–.265 | 420–430 | .17–.22 | .09–.10 | .07–.08 | 9.7–13.7 |
| 178–202 | 1.0 | .187 | 160 | .13 | .13 | .07 | 13.5–15 |
| 202–266 | .6–1.1 | .12–.14 | 28–48 | .1–.11 | .09–.175 | .077 | 15–20.1 |

EXAMPLE II

In this example, *Xanthomonas campestris* P-107 ATCC 31602 was grown in continuous culture in a minimal medium of the composition given in Table IV. This strain, after initial isolation, was maintained on agar slants of EMSY-1 medium (see Table II) at 4° C. The culture was transferred to fresh slants of the same medium at biweekly intervals. Inoculation procedures were essentially the same as in Example I except for the following changes: two 10 ml volumes of EMSY-1 broth contained in 16 by 25 mm tubes were inoculated from a slant culture (F 3 days old) of strain ATCC 31602, and incubated at 150 rpm at 28° C. on a rotary shaker at a 20° inclination for 24 hours. Cultures were then separately inoculated into two 50 ml volumes of minimal medium (Table IV) which also contained 4 gm/liter of phosphate buffer at pH 7.0. The 50 ml cultures were incubated in 1000 ml Erlenmeyer flasks at 28° C. and 250 rpm for 36 hours. Then the two 50 ml cultures were used to separately inoculate two 500 ml volumes of the same medium contained in 2800 ml Fernbach flasks. These were also incubated at 28° C. and 250 rpm for 36 hours. At the time of inoculation, the cell concentration was 1.0 gm/liter. The culture was inoculated into 20 liters of the same medium in a 28 liter fermenter and initial operating conditions were identical to those in Example I. After a 40-hour lag, the culture grew in a batch mode for 30 hours and reached a cell concentration of 0.77 gm/liter. At this point, continuous culture was started using the same medium at a dilution rate of 0.035 hr$^{-1}$. During continuous opera-

EXAMPLE III

Strain P-107 was again grown in minimal medium of the same composition as in Example II, but adjusted so as to yield about 1 gram per liter cell concentration. The innoculation preparation procedure was changed from Example II as follows: a loopful of culture from a fresh (<3 day old) slant culture was transferred to 50 ml of half strength YM broth (Difco) contained in a 1000 ml Erlenmeyer flask and incubated for 24 hours at 28° C. and 250 rpm. The 50 ml culture was then transferred to 400 ml of half strength YM broth contained in a 2800 ml Fernbach flask and incubated at 28° C. and agitated at 250 rpm for 24 hours. This culture was then added to 2000 ml of minimal medium contained in a 5-liter continuous fermenter (Fermentation Design Model MAO 5 Fl). The actual composition of the medium employed is given in Table XII.

TABLE XII

| Component | Amount (per liter) |
|---|---|
| NH$_4$Cl | 0.5 gm |
| Glucose | 10.0 gm |
| Citric Acid | 0.3 gm |
| H$_3$PO$_4$ | 0.17 gm |
| MgSO$_4$ | 0.06 gm |
| CaCl$_2$ | 0.06 gm |
| FeSO$_4$ | 2.7 mg |
| ZnSO$_4$ | 0.8 mg |
| MnSO$_4$ | 0.27 mg |

TABLE XII-continued

| Component | Amount (per liter) |
|---|---|
| Na$_2$MoO$_4$ | 0.14 mg |
| H$_3$BO$_3$ | 0.19 mg |
| KI | 0.04 mg |
| CuSO$_4$ | 0.5 mg |

During continuous operation the temperature was held at 28° C., the pH at 7.0, the air rate was 0.9 vol/vol/min, the agitation rate was 400 rpm and the dilution rate during the operation ranged from 0.031 to 0.09 hr$^{-1}$. After an initial delay of 24 hours, the specific productivity increased to 0.2–0.31 gm/gm cells/hour for almost 200 hours. Thereafter mechanical problems forced the unit to be put back in a batch mode for about 50 hours. After restoring normal operation, the culture eventually improved the specific productivity back to 0.19–0.25 gm/gm cells/hour. The results of this run are summarized in Table XIII below.

TABLE XIII

| Time Period (Hrs) | Cell Conc'n (gm/l) | Xanthan Conc'n (%) | Viscosity (cp) | Xanthan Volumetric Productivity (gm/l/hr) | Xanthan Specific Productivity (gm/gm cells/hr) | Dilution Rate (hr$^{-1}$) | Culture Turnover (Q) |
|---|---|---|---|---|---|---|---|
| 0–24 | 1.22 | 0.38 | 800 | .22 | .18 | .059 | 1.4 |
| 24–144 | .82–.87 | 0.26–.37 | 520–700 | .19–.26 | .24–.31 | .069–.076 | 1.4–10 |
| 144–216 | .8–1.06 | .25–.35 | 160–800 | .16–.23 | .20–.23 | .062–.065 | 10–14.5 |
| 216–264 | Mechanical problems; culture upset; unit on batch | | | | | | |
| 264–384 | 1.2–2.6 | .12–.27 | 30–600 | .02–.09 | .07–.16 | .031–.039 | 14.5–19.5 |
| 384–509 | 2.03–1.3 | .31–.37 | 420–620 | .23–31 | .09–.25 | .06–.09 | 19.5–28.5 |

The data show that strain P-107 has a high specific productivity which it maintains without culture degeneration even after a severe upset in the culture which lasted two days. Also, the results indicate that good specific productivity can be maintained even at relatively low cell concentration.

It will be apparent from the foregoing description that by the use of the above-mentioned novel strain it is now possible to design and operate a long-term continuous culture process for xanthan production in which the culture does not degrade, cheap simple media are used, and xanthan can be produced at a high specific productivity, thus lowering the overall economics of the process.

We claim:

1. A method for the production of a heteropolysaccharide which comprises continuously culturing a degenerative resistant strain of bacteria designated Xanthomonas campestris P-107 having the identifying characteristics of ATCC 31602, in an aqueous nutrient medium comprising essentially assimilable sources of carbon, nitrogen, and inorganic substances, wherein said medium is continuously fed to a fermentation zone to produce said polysaccharide, and withdrawing the resulting fermented medium from said zone.

2. The method of claim 1 in which said medium is a minimal medium.

3. The method of claim 2 wherein said minimal medium also contains as a complex nitrogen source, one of the group consisting of yeast extract and yeast autolysate.

4. The method of claim 1 in which the fermentation is conducted at a specific xanthan productivity in excess of 0.2 gm xanthan/gm cells/hr.

5. The method of claim 1 wherein said fermented medium is withdrawn from said zone at a rate such that an essentially steady state condition is maintained in said zone.

6. A method for the production of a heteropolysaccharide which comprises continuously culturing a degenerative resistant strain of Xanthomonas campestris P-107 having the identifying characteristics of ATCC 31602 in a minimal medium containing a growth limiting nutrient and wherein said medium is continuously fed to a first fermentation zone to produce additional amounts of said strain together with said heteropolysaccharide, thereafter transferring the effluent from said first zone to a second fermentation zone, and adding a fermentable sugar to said effluent in said second zone whereby the formation of heteropolysaccharide in said second zone is maximized.

7. The method of claim 6 in which the fermentable sugar employed is glucose.

8. The method of claim 1 or 6 in which the heteropolysaccharide is xanthan.

9. A biologically pure culture of a novel strain of Xanthomonas campestris P-107 having the identifying characteristics of ATCC 31602, said strain being capable of producing xanthan gum in recoverable amounts upon fermentation of an aqueous nutrient medium containing assimilable sources of carbon, nitrogen and inorganic substances and being resistant to cell degeneration when subjected to continuous fermentation conditions.

10. A biologically pure culture consisting essentially of Xanthomonas campestris P-107 ATTC 31602.

11. A biologically pure culture consisting essentially of Xanthomonas campestris P-107 ATCC 31602, said culture being degenerative resistant when continuously cultured in an aqueous nutrient medium, and capable of producing xanthan gum in good yields.

12. A bacterial culture consisting essentially of Xanthomonas campestris P-107 ATTC 31602.

13. A bacterial culture consisting essentially of Xanthomonas campestris P-107 ATTC 31602, said culture being degenerative resistant when continuously cultured in an aqueous nutrient medium, and capable of producing xanthan gum in good yields.

14. A bacterial culture consisting essentially of Xanthomonas campestris P-107 ATTC 31602, said culture capable of producing xanthan gum in recoverable amounts upon fermentation of an aqueous nutrient medium containing assimilable sources of carbon, nitrogen, and inorganic substances.

* * * * *